United States Patent [19]

Sakurai et al.

[11] 4,137,196
[45] Jan. 30, 1979

[54] GELATINOUS FRAGRANCE-IMPARTING COMPOSITION CONTAINING STABILIZED PERFUME

[75] Inventors: Akira Sakurai, Sakura; Manabu Fujita, Kashiwa, both of Japan

[73] Assignee: Kao Soap Co., Ltd., Tokyo, Japan

[21] Appl. No.: 898,129

[22] Filed: Apr. 20, 1978

[30] Foreign Application Priority Data

May 23, 1977 [JP] Japan .................................. 52-59572

[51] Int. Cl.² ................................................ C11B 9/00
[52] U.S. Cl. ..................................... 252/522; 423/312
[58] Field of Search .......................................... 252/522

[56] References Cited

U.S. PATENT DOCUMENTS

| | | | |
|---|---|---|---|
| 3,385,713 | 5/1968 | Levinson et al. | 252/522 |
| 3,565,559 | 2/1971 | Sato et al. | 252/522 |
| 3,849,326 | 11/1974 | Jaggers et al. | 252/522 |

*Primary Examiner*—Veronica O'Keefe
*Attorney, Agent, or Firm*—Blanchard, Flynn, Thiel, Boutell & Tanis

[57] ABSTRACT

A gelatinous fragrance-imparting composition comprising a gel substrate, a perfume, at least one first additive selected from the group consisting of phosphates having the formula:

$$(M)_m(H)_{3-m}PO_4 \cdot xH_2O \qquad (I)$$

wherein M is sodium, potassium or ammonium, m is an integer of from 1 to 3, and x is 0 or an integer of from 1 to 12, and carbonates having the formula:

$$(M)_n(H)_{2-n}CO_3 \cdot xH_2O \qquad (II)$$

wherein M and x are as defined above and n is an integer of 1 or 2, and at least one pH adjusting agent selected from phosphates and carbonates having the above formulas (I) and (II), with the proviso that said pH adjusting agent is different from said first additive, and wherein the pH of the composition is in the range of from 6.0 to 10.0.

7 Claims, No Drawings

GELATINOUS FRAGRANCE-IMPARTING COMPOSITION CONTAINING STABILIZED PERFUME

BACKGROUND OF THE INVENTION

1. Field of the Invention

The present invention relates to a gelatinous fragrance-imparting composition in which a perfume is incorporated as an active ingredient in a gel, in such a manner that the perfume remains stable for a long time.

A gelatinous fragrance-imparting composition comprises, as a gel substrate, a water-soluble macromolecular compound such as carrageenan, agar, an alginate, guaiac gum, locust bean gum, gelatin, casein, polyvinyl alcohol, polyethylene oxide, a polyacrylate or the like, and a perfume is dispersed and retained in the gel substrate. When water is evaporated from the composition, the perfume is evaporated into the open air together with the evaporated water, whereby to produce an aromatizing effect. In general, such gelatinous fragrance-imparting composition comprises 1.0 to 5.0% by weight of gel substrate, 0.1 to 20.0% by weight of a perfume and 0.1 to 20% by weight of a water-soluble surface active agent, with the balance being essentially water. When a perfume is emulsified and dispersed in such an aqueous gel, the stability of some perfumes is very bad and a change of the fragrance or a generation of a bad smell often occurs during long-time storage. Especially, simple perfumes of the ester and the aldehyde types, such as linalyl acetate, benzyl acetate and cyclamen aldehyde, possess very low stabilities in such compositions. Since these simple perfumes are employed as basic perfume ingredients when blended perfume compositions are prepared, this poor stability results in various limitations on the generation of pleasant smells having special desired characteristics.

SUMMARY OF THE INVENTION

We have discovered that the stability of a perfume incorporated in such aqueous gel compositions can be improved when a specific phosphate or carbonate is incorporated in an aqueous gel having a perfume emulsified and/or dispersed therein and when the pH of the gel is adjusted to 6.0 to 10.0 by the addition of an appropriate pH adjusting agent. Based on this finding, we have now completed the present invention.

More specifically, in accordance with the present invention, there is provided a stable, gelatinous, fragrance-imparting composition comprising a gel substrate, a perfume, at least one first additive selected from the group consisting of phosphates having the formula:

$$(M)_m(H)_{3-m}PO_4 \cdot xH_2O \qquad (I)$$

wherein M is sodium, potassium or ammonium, m is an integer of from 1 to 3, and x is 0 or an integer of from 1 to 12, and carbonates having the formula:

$$(M)_n(H)_{2-n}CO_3 \cdot xH_2O \qquad (II)$$

wherein M and x are the same as defined above and n is an integer of 1 or 2, and at least one pH adjusting agent selected from phosphates and carbonates having the above formulas (I) and (II), with the proviso that said pH adjusting agent is different from said first additive, and wherein the pH of the composition is in the range of from 6.0 to 10.0.

As the phosphates represented by the formula (I), there can be mentioned, for example, monoammonium dihydrogen phosphate, diammonium monohydrogen phosphate, triammonium phosphate, monosodium dihydrogen phosphate, disodium monohydrogen phosphate, trisodium phosphate, monopotassium dihydrogen phosphate, dipotassium monohydrogen phosphate and tripotassium phosphate.

As the carbonates represented by the formula (II), there can be mentioned, for example, ammonium hydrogen carbonate, ammonium carbonate, sodium hydrogen carbonate, sodium carbonate, potassium hydrogen carbonate and potassium carbonate.

In the present invention, as the gel substrate there can be employed the above-mentioned natural and synthetic water-soluble macromolecular compounds (industrial gums) such as carrageenan, agar, alginates, guaiac gum, locust bean gum, gelatin, casein, polyvinyl alcohol, polyethylene oxide, polyacrylates and the like.

As simple perfumes which have an especially prominent effect in the present invention, there can be mentioned p-cresyl methyl ether, isoeugenol, octyl aldehyde, alkyl aldehydes having 12 to 26 carbon atoms in the alkyl group, benzaldehyde, hyacinth aldehyde, cinnamic aldehyde, jasmine aldehyde, lily aldehyde, 1-carvone, jasmone, linalyl acetate, linalyl formate, methyl benzoate, civet, isopropyl quinoline, p-methyl quinoline, dimethylbenzyl carbinol, ethyl acetate, pineapple oil, mellon natural, coffee oil base, methyl citronellal and acetaldehyde.

According to the present invention, a small amount of a phosphate or a carbonate represented by the above formulas (I) and (II) is added to an aqueous gel having a perfume incorporated therein and at least one different phosphate or carbonate represented by the above formulas (I) and (II) is added to the composition whereby to obtain a fragrance-imparting composition in which the pH is in the range of from 6.0 to 10.0. For example, when only trisodium phosphate is added to such an aqueous gel, the pH of the composition is about 12, and then monoammonium dihydrogen phosphate is added to the composition to adjust the pH to 7 to 8. In the present invention, these inorganic phosphate and carbonate salts perform a kind of a buffering action and the pH of the gel is stably maintained at a certain level and reduction of the pH caused by external influences or deterioration or decomposition of the perfume is prevented. As a result, deterioration or decomposition of the perfume can be prevented and change of the fragrance does not occur at all. Adjustment of the initial pH of the gel to be in the range of from 6 to 10 may be attained by selecting a single appropriate compound among the phosphates and carbonates represented by the above formulas (I) and (II), but in this case, the pH stability is extremely poor and the pH drastically changes caused by external influences or on initiation of deterioration or decomposition of the perfume, and it is impossible to retain the perfume in a stable condition in the gel.

The gelatinous fragrance-imparting composition of the present invention is effective when the pH of the composition is in the range of from 6.0 to 10.0, and an especially good result is obtained when the pH is close to neutral, namely, from 7.0 to 8.0. The amount of the carbonate or phosphate used as the first additive can be small, and the intended effect is sufficiently attained when the first additive is added in an amount of from 0.01 to 10.0% by weight, preferably 0.1 to 1.0% by weight, based on the total weight gelatinous fragrance-imparting composition. The phosphate or carbonate employed as the pH adjusting agent (second additive) is added in an amount necessary for adjusting the pH of the composition to 6.0 to 10.0.

In the gelatinous fragrance-imparting composition of the present invention, anionic surface active agents, non-ionic surface active agents, cationic surface active agents and amphoteric surface active agents may be used to emulsify and disperse the perfume, according to need. As the anionic surface active agent, there can be mentioned, for example, higher fatty acid salts, higher alcohol sulfuric acid esters, alkyl benzene-sulfonic acid salts, alkyl naphthalene-sulfonic acid salts, alkyl phosphate salts and polyoxyethylene alkyl sulfate salts. As the non-ionic surface active agent, there can be mentioned, for example, polyoxyethylene alkyl ethers, polyoxyethylene alkyl phenyl ethers, sorbitan fatty acid esters, polyoxyethylene sorbitan fatty acid esters, polyoxyethylene acyl esters and fatty acid monoglycerides. As the cationic surface active agent, there can be mentioned, for example, alkyl amine salts, quaternary ammonium salts and polyoxyethylene alkyl amines. As the amphoteric surface active agent, there can be mentioned, for example, alkyl betaines and imidazolines. In addition, there may be added a dye and a solvent such as ethanol, isopropanol, glycerin, glycol or the like.

The composition of the gelatinous fragrance-imparting composition of the present invention comprises (a) 0.3 to 10.0% by weight, preferably 1.0 to 3.0% by weight, of gel substrate, (b) 0.1 to 20% by weight, preferably 2.0 to 7.0% by weight, of a perfume, (c) 0.01 to 10% by weight, preferably 0.1 to 1.0% by weight, of said first phosphate or carbonate additive, (d) 0.005 to 10.0% by weight, preferably 0.1 to 1.0% by weight, of a pH adjusting agent and (e) 0 to 20% by weight, preferably 1.0 to 7.0% by weight, of a surface active agent, with (f) the balance being essentially water.

The present invention will now be described in more detail by reference to the following illustrative Examples, in which all references to "%" and "parts" are by weight.

EXAMPLE 1

2.0 Parts of carrageenan was homogeneously dispersed in deionized water. To the dispersion there was added either an aqueous solution of a predetermined amount of only one salt as the first additive or an aqueous solution containing predetermined amounts of a salt as the first additive and containing a different salt as the pH adjusting agent. The mixture was heated at 75° C. to form a homogeneous solution and the solution was cooled to 60° C. Then, 2.0 parts of polyoxyethylene (20) sorbitan monolaurate and a perfume (1.0% of linalyl acetate as a simple perfume, based on the total composition, or 5.0% of a citrus compounded perfume, based on the total composition) were added to the solution, and the mixture was poured into a vessel and cooled to room temperature whereby to obtain a gelatinous fragrance-imparting composition.

The change of the fragrance of this gelatinous composition was examined and evaluated in the following manner.

The gelatinous composition was stored at 40° C. for 20 days and the fragrance was organoleptically evaluated by a panel of four perfume compounding experts, based on the following evaluation criteria:

◉ : no change of the fragrance
○ : a slight change of the fragrance was observed
Δ : a significant change of the fragrance was observed
X : the fragrance was completely changed The results obtained when only the first additive was used, but no pH adjusting agent was used, are shown in Table 1. The results obtained when both the first additive and the pH adjusting agent were added are shown in Table 2.

In these Tables, the gel pH is the pH value of a 10% aqueous solution of the gelatinous composition.

The sample which had been stored at 40° C. for 20 days was formed into a 10% aqueous solution and the pH of the solution was measured. The residual amount of linalyl acetate in the solution was determined according to gas chromatography (FID) using a silicone type column. The results obtained are shown in Table 3.

Table 1

| Additive | Amount Added (%) | Gel pH | Organoleptic Evaluation after Storage | |
|---|---|---|---|---|
| | | | Simple perfume | compounded perfume |
| Phosphates | | | | |
| ammonium dihydrogen phosphate | 1.0 | 4.5 | X | X |
| sodium dihydrogen phosphate | 1.0 | 4.5 | X | X |
| potassium dihydrogen phosphate | 1.0 | 4.6 | X | X |
| diammonium monohydrogen phosphate | 1.0 | 9.3 | Δ | Δ |
| disodium monohydrogen phosphate | 1.0 | 9.2 | Δ | Δ |
| trisodium phosphate | 1.0 | 12.2 | Δ | Δ - X |
| tripotassium phosphate | 1.0 | 12.2 | Δ | X |
| Sulfates | | | | |
| ammonium sulfate | 1.0 | 6.2 | X | Δ - X |
| sodium sulfate | 1.0 | 6.0 | Δ - X | Δ - X |
| potassium sulfate | 1.0 | 8.0 | Δ | X |
| ammonium hydrogen sulfate | 0.05 | 4.0 | X | X |
| sodium hydrogen sulfate | 0.05 | 4.2 | X | X |
| Carbonates | | | | |
| ammonium carbonate | 1.0 | 7.95 | Δ | Δ |
| sodium carbonate | 1.0 | 8.4 | | Δ |
| potassium carbonate | 1.0 | 11.1 | Δ | Δ |
| ammonium hydrogen carbonate | 1.0 | 8.1 | | Δ |
| sodium hydrogen carbonate | 1.0 | 8.4 | | |
| potassium hydrogen carbonate | 1.0 | 8.4 | Δ | Δ |
| Other Salts | | | | |
| ammonium chloride | 1.0 | 6.8 | Δ - X | X |
| sodium chloride | 1.0 | 6.0 | Δ - X | X |
| potassium chloride | 1.0 | 6.4 | Δ - X | X |

Table 1-continued

| Additive | Amount Added (%) | Gel pH | Organoleptic Evaluation after Storage Simple perfume | compounded perfume |
|---|---|---|---|---|
| not added | 0 | 6.8 | × | × |

Table 2

| First Additive | | pH Adjusting Agent | | | Organoleptic Evaluation after Storage | |
|---|---|---|---|---|---|---|
| Kind | Amount (%) | Kind | Amount (%) | Gel pH | simple perfume | compounded perfume |
| Present Invention | | | | | | |
| Na$_2$PO$_4$ . 2H$_2$O | 0.312 | Na$_2$HPO$_4$ . 12H$_2$O | 0.537 | 6.5 | ◉ | ◉ |
| KH$_2$PO$_4$ | 0.136 | Na$_2$HPO$_4$ 12H$_2$O | 2.03 | 7.6 | ◉ | ◉ |
| K$_2$HPO$_4$ | 0.348 | NH$_4$H$_2$PO$_4$ | 0.109 | 8.2 | ◉ | ◉ |
| Na$_3$PO$_4$ . 12H$_2$O | 0.532 | NH$_4$H$_2$PO$_4$ | 0.230 | 7.4 | ◉ | ◉ |
| NaHCO$_3$ | 0.504 | Na$_2$CO$_3$ | 0.212 | 9.5 | ◉ | ◉ |
| KHCO$_3$ | 0.20 | K$_2$CO$_3$ | 0.00345 | 9.0 | ◉ | ◉ |
| NH$_4$HCO$_3$ | 0.0395 | (NH$_4$)$_2$CO$_3$ | 0.158 | 8.0 | ◉ | ◉ |
| Comparisons | | | | | | |
| NaHCO$_3$ | 0.042 | Na$_2$CO$_3$ | 0.503 | 11.0 | ◯ | ◯ |
| KHCO$_3$ | 0.2 | K$_2$CO$_3$ | 0.087 | 10.5 | ◯ | ◯ |
| Na$_2$HPO$_4$ . 12H$_2$O | 0.716 | NaHSO$_4$ | 0.0241 | 7.8 | × | × |
| NH$_4$HSO$_4$ | 0.23 | NaOH | 0.094 | 9.0 | × | × |
| KHSO$_4$ | 0.272 | KOH | 0.206 | 11.0 | × | × - △ |
| NaHSO$_4$ | 0.276 | NaOH | 0.085 | 9.5 | × | × |
| NH$_4$HSO$_4$ | 0.23 | NaOH | 0.083 | 8.1 | △ - × | × |
| NH$_4$HSO$_4$ | 0.23 | KOH | 0.113 | 8.2 | × | × |
| trisodium citrate | 0.516 | Na$_2$SO$_4$ | 0.272 | 8.2 | × | × |
| trisodium citrate | 0.0116 | (NH$_4$)$_2$SO$_4$ | 0.27 | 7.8 | × | × |
| trisodium citrate | 3.176 | KCl | 0.35 | 9.2 | × | × |
| trisodium citrate | 0.0477 | NaCl | 0.7 | 8.3 | × | × |
| not added | 0 | not added | 0 | 6.8 | × | × |

Table 3

| Additive Salt | pH Adjusting Agent | pH just after preparation | pH after storage | Residual Amount (%) of linalyl acetate, based on starting amount |
|---|---|---|---|---|
| Comparisons | | | | |
| not added | — | 6.8 | 5.1 | 32.5 |
| sodium sulfate | — | 6.0 | 5.0 | 31.4 |
| potassium sulfate | — | 8.0 | 4.8 | 35.4 |
| potassium dihydrogen phosphate | — | 9.3 | 4.9 | 39.7 |
| ammonium hydrogen carbonate | — | 8.1 | 5.2 | 41.0 |
| disodium citrate | — | 6.9 | 4.8 | 39.0 |
| ammonium hydrogen sulfate | sodium hydroxide | 9.0 | 5.0 | 31.6 |
| potassium hydrogen sulfate | potassium hydroxide | 11.0 | 5.2 | 30.1 |
| ammonium hydrogen sulfate | sodium hydroxide | 8.1 | 4.9 | 32.3 |
| Present Invention | | | | |
| potassium dihydrogen phosphate | disodium hydrogen phosphate | 6.5 | 6.3 | 65.7 |
| dipotassium hydrogen phosphate | ammonium dihydrogen phosphate | 8.2 | 7.8 | 59.1 |
| sodium carbonate | sodium hydrogen carbonate | 9.5 | 9.1 | 60.5 |
| potassium hydrogen carbonate | potassium carbonate | 9.0 | 8.9 | 61.1 |

As will be apparent from the results shown in the Tables, when only one phosphate, carbonate, sulfate or other inorganic salt is added, if the pH of the composition is in the range of from 6 to 10 in the initial stage, the fragrance stability is not improved. In contrast, when a phosphate or carbonate of the present invention is added and a second and different phosphate or carbonate is added to adjust the pH of the composition to 6.0 to 10.0, the fragrance is not changed even after longtime storage, and from the gas chromatography analysis, it is confirmed that decomposition of the perfume is reduced and the residual amount of the perfume is high.

EXAMPLE 2

In 84.8 parts of deionized water there were incorporated 0.15 part of monopotassium dihydrogen phosphate and 0.15 part of disodium monohydrogen phosphate, and the mixture was heated at 90° C. to dissolve the salts. Then, 2.0 parts of agar as the gel substrate, 3.0 parts of sodium dodecylbenzenesulfonate, 3.0 parts of a perfume (green compounded perfume or ester aldehyde simple perfume) and 5.0 parts of ethanol were added to the above solution under agitation, and the mixture was poured into a vessel and cooled to room temperature to solidify same whereby to form a gelatinous aromatizing agent.

After storage at 40° C. for 20 days, the organoleptic test was carried out in the same manner as described in Example 1. It was found that the fragrance was not significantly changed.

EXAMPLE 3

A gelatinous aromatizing agent was prepared from 1.5 parts of carrageenan as a gel substrate, 2.0 parts of a polyoxyethylene alkyl ether, 2.0 parts of a perfume (ester type green compounded perfume), 2.3 parts of sodium hydrogen carbonate, 2.5 parts of sodium carbonate and 89.7 parts of deionized water in the same manner as described in Example 1. When the organoleptic test was carried out in the same manner as described in Example 1, it was found that the fragrance was not significantly changed and good results were obtained.

EXAMPLE 4

This Example illustrates an embodiment wherein an alginic acid derivative is used as a gel substrate.

A basic composition comprising 2.0 parts of an alginic acid derivative (AG-1), 2.0 parts of a surface active agent (polyoxyethylene alkyl phenyl ether) and 3.0 parts of a perfume (floral compounded perfume) was incorporated into 93.0 parts of deionized water to form a comparative gelatinous aromatizing agent. Separately, 0.6 part of a sodium dihydrogen phosphate dihydrate and 0.5 part of disodium monohydrogen phosphate dodecahydrate were added to the above basic composition, and the mixture was added to 91.9 parts of deionized water to form an aromatizing agent according to the present invention. After these samples had been stored at 40° C. for 20 days, the organoleptic test was carried out in the same manner as described in Example 1. In case of the sample according to the present invention, the fragrance was not significantly changed and good results were obtained.

EXAMPLE 5

This Example illustrates an embodiment where gelatin was used as a gel substrate.

A basic composition comprising 2.5 parts of gelatin, 2.5 parts of a surface active agent (polyoxyethylene fatty acid ester) and 1.5 parts of a perfume (green floral compounded perfume) was added to 93.5 parts of deionized water to form a comparative gel. Separately, 2 parts of potassium hydrogen carbonate and 0.03 part of potassium carbonate were added to the above basic composition, and the mixture was added to 91.47 parts of deionized water to form a sample according to the present invention.

After these samples had been stored at 40° C. for 20 days, the organoleptic test was carried out in the same manner as described in Example 1. In case of the sample according to the present invention, the fragrance was not significantly changed and good results were obtained.

The embodiments of the invention in which an exclusive property or privilege is claimed are defined as follows:

1. A gelatinous fragrance-imparting composition comprising a gel substrate, a perfume, at least one first additive selected from the group consisting of phosphates having the formula:

$$(M)_m(H)_{3-m}PO_4 \cdot xH_2O \qquad (I)$$

wherein M is sodium, potassium or ammonium, m is an integer of from 1 to 3, and x is 0 or an integer of from 1 to 12, and carbonates having the formula:

$$(M)_n(H)_{2-n}CO_3 \cdot xH_2O \qquad (II)$$

wherein M and x are the same as defined above and n is an integer of 1 or 2, and at least one pH adjusting agent selected from said phosphates and carbonates, with the proviso that said pH adjusting agent is different from said first additive, and wherein the pH of said composition is in the range of from 6.0 to 10.0.

2. A composition as set forth in claim 1, wherein the amount of said first additive is 0.01 to 10.0% by weight, based on the total weight of said composition.

3. A composition as set forth in claim 2, wherein the amount of said first additive is 0.1 to 1.0% by weight, based on the total weight of said composition.

4. A composition as set forth in claim 3, wherein the pH is in the range of from 7.0 to 8.0.

5. A composition as set forth in claim 1, consisting essentially of (a) from 0.3 to 10% by weight of water-soluble gel substrate selected from the group consisting of carrageenan, agar, alginates, guaiac gum, locust bean gum, gelatin, casein, polyvinyl alcohol, polyethylene oxide and polyacrylates, (b) from 0.1 to 20% by weight of perfume selected from the group consisting of p-cresyl methyl ether, isoeugenol, octyl aldehyde, alkyl aldehydes having 12 to 26 carbon atoms in the alkyl group, benzaldehyde, hyacinth aldehyde, cinnamic aldehyde, jasmine aldehyde, lily aldehyde, 1-carvone, jasmone, linalyl acetate, linalyl formate, methyl benzoate, civet, isopropyl quinoline, p-methyl quinoline, dimethylbenzyl carbinol, ethyl acetate, pineapple oil, mellon natural, coffee oil base, methyl citronellal and acetaldehyde, (c) from 0.01 to 10% by weight of said first additive, (d) from 0.005 to 10% by weight of said pH adjusting agent, (e) from 0 to 20% by weight of water-soluble organic surfactant effective to emulsify and disperse said perfume, and (f) the balance is essentially water.

6. A composition as set forth in claim 5, consisting essentially of from 1.0 to 3.0% by weight of (a), from 2.0 to 7.0% by weight of (b), from 0.1 to 1.0% by weight of (c), from 0.1 to 1.0% by weight of (d), from 1.0 to 7.0% by weight of (e) and the balance is essentially water.

7. A composition as set forth in claim 5 in which said first additive and said pH adjusting agent both are phosphates of formula (I) or carbonates of formula (II).

* * * * *